(12) United States Patent
Arnold

(10) Patent No.: US 10,456,335 B2
(45) Date of Patent: Oct. 29, 2019

(54) ORAL HYGIENE COMPOSITIONS AND METHODS

(71) Applicant: Carson Laboratories, I.P., Inc., Las Vegas, NV (US)

(72) Inventor: Michael Arnold, Beverly Hills, CA (US)

(73) Assignee: 90 Seconds to Wow, LLC, Irvine, CA (US)

( * ) Notice: Subject to any disclaimer, the term of this patent is extended or adjusted under 35 U.S.C. 154(b) by 0 days.

(21) Appl. No.: 14/456,953

(22) Filed: Aug. 11, 2014

(65) Prior Publication Data

US 2015/0004560 A1 Jan. 1, 2015

Related U.S. Application Data

(63) Continuation-in-part of application No. 12/061,493, filed on Apr. 2, 2008, now Pat. No. 8,801,436.

(51) Int. Cl.
| | | |
|---|---|---|
| *A61K 8/04* | (2006.01) | |
| *A61K 8/22* | (2006.01) | |
| *A61K 8/365* | (2006.01) | |
| *A61K 8/34* | (2006.01) | |
| *A61K 8/19* | (2006.01) | |
| *A61K 8/25* | (2006.01) | |
| *A61K 8/24* | (2006.01) | |
| *A61Q 11/00* | (2006.01) | |
| *A61C 19/06* | (2006.01) | |
| *A61K 8/38* | (2006.01) | |

(52) U.S. Cl.
CPC ............ *A61K 8/046* (2013.01); *A61C 19/066* (2013.01); *A61K 8/22* (2013.01); *A61K 8/38* (2013.01); *A61Q 11/00* (2013.01); *A61K 2800/87* (2013.01)

(58) Field of Classification Search
USPC .............................. 424/466; 433/216; 426/74
See application file for complete search history.

(56) References Cited

U.S. PATENT DOCUMENTS

| | | | | |
|---|---|---|---|---|
| 5,853,759 A | * | 12/1998 | Katdare | ............... A61K 9/0007 424/466 |
| 6,224,917 B1 | * | 5/2001 | Murto | .................. A23K 1/1603 426/392 |
| 7,458,464 B1 | * | 12/2008 | Kutsch | ..................... A46B 9/04 206/570 |
| 2006/0034921 A1 | * | 2/2006 | Katdare | ............... A61K 9/1617 424/466 |

* cited by examiner

*Primary Examiner* — Walter Webb
(74) *Attorney, Agent, or Firm* — Vegh IP Legal; Stephen Z. Vegh

(57) ABSTRACT

Disclosed are methods, compositions and kits for whitening teeth and promoting better oral hygiene. A one-step protocol is disclosed in which concentrated hydrogen peroxide is delivered into the oral cavity by aerosol spray, without burning, discomfort or damage to the soft tissues of the mouth. A two-step protocol is also disclosed in which an effervescent powder formulation is included as a post-treatment following the aerosol spray. In some embodiment, the powder formulation can be used alone to promote remineralization, reduce plaque, reduce bacterial count and generally enhance oral hygiene.

21 Claims, 8 Drawing Sheets

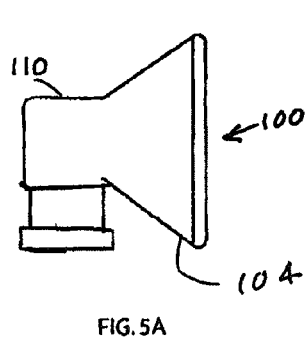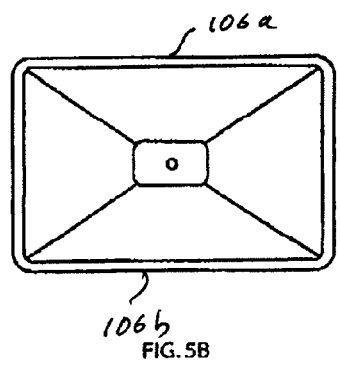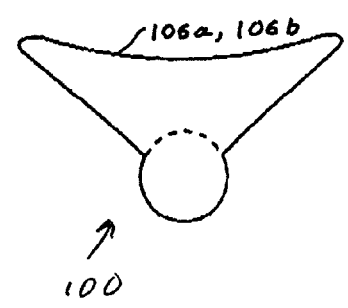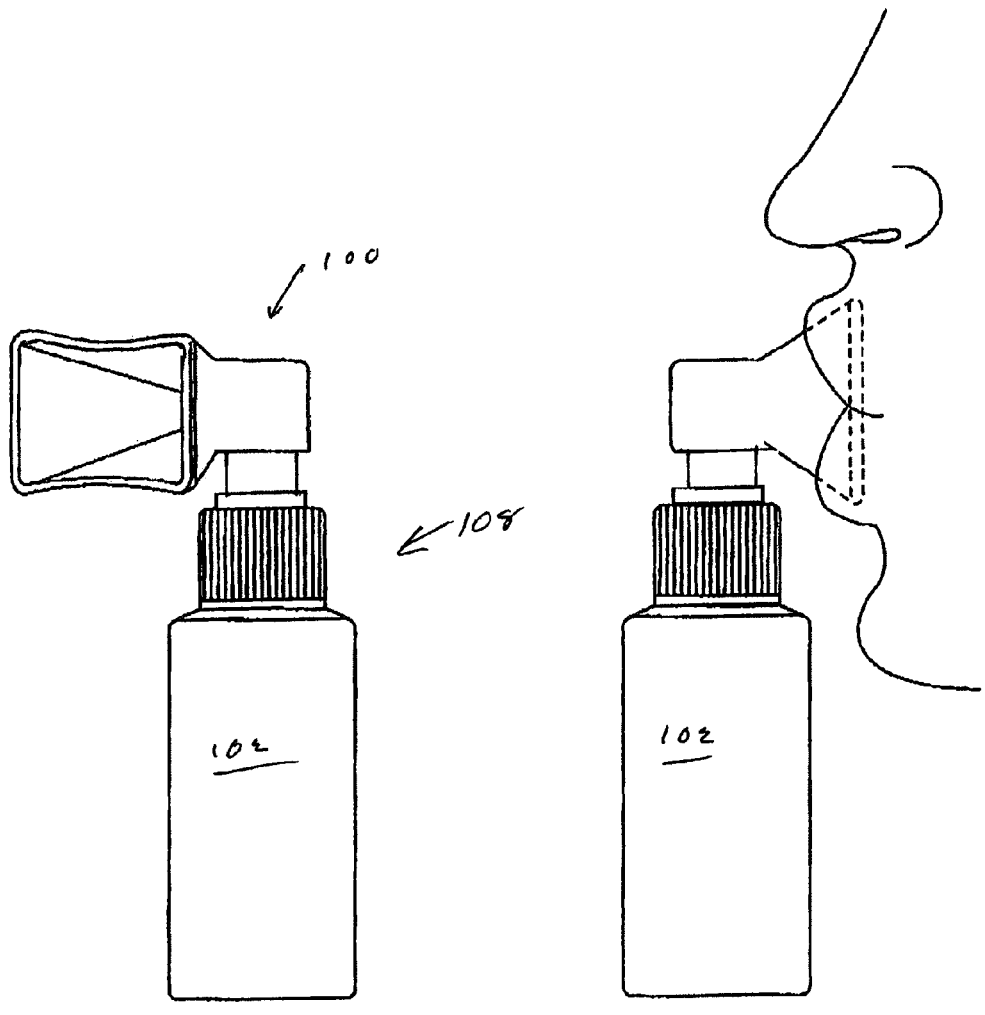
FIG. 5A  FIG. 5B  FIG. 5C
FIG. 5D  FIG. 5E

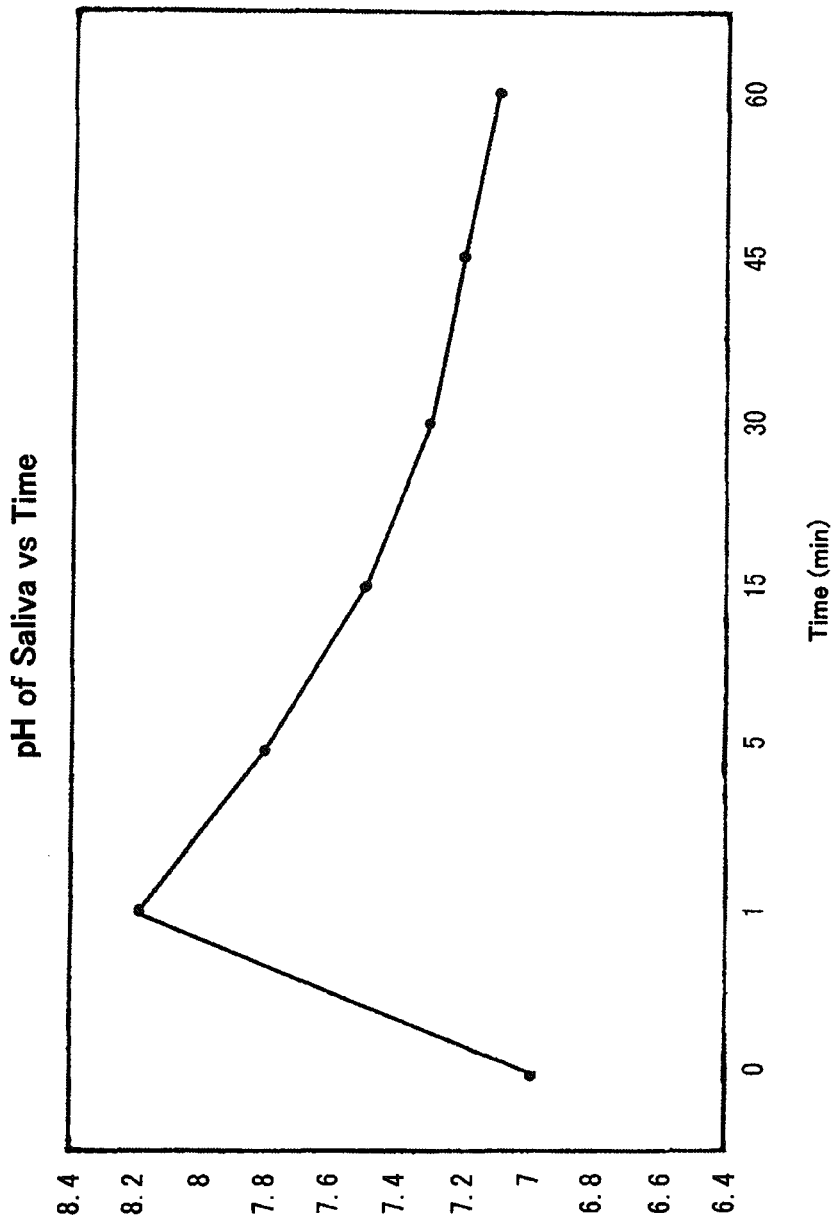

ORAL HYGIENE COMPOSITIONS AND METHODS

RELATED APPLICATIONS

This application is a continuation-in-part application of U.S. application Ser. No. 12/061,493 filed on Apr. 2, 2008.

BACKGROUND

The development of tooth whitening techniques has been taking place for well over 100 years. It is well known that the teeth can be effectively bleached by the use of hydrogen peroxide as the bleaching agent, and it is proven that, in general, tooth-whitening preparations having higher concentrations of bleaching agent are more effective in whitening the teeth than those of lower concentrations. Thus, increasing concentrations of the bleaching agent gives rise to a more rapid bleaching action.

A problem with the high concentrations of bleaching solutions is that to perform safe teeth bleaching operations, a "dam" must be prepared to cover the soft tissue in order to keep such insulated and protected from damage as a result of the vigorous oxidative damage that would occur if these concentrated hydrogen peroxide solutions made physical contact with the gingival tissues. Application of concentrated solutions of hydrogen peroxide, without using gel formulations (to provide slower release of lower concentrations of hydrogen peroxide) and a dam (to minimize contact with soft tissues) results in severe discomfort, blistering and tissue injury. Indeed, oral rinse preparations of hydrogen peroxide having concentrations greater than 6% are dangerous for use in the human oral cavity, since exposure of the oral soft tissues for times on the order of seconds, has been demonstrated to cause immediate injury to the gingival and soft tissue of the human oral cavity. The greater the concentration of hydrogen peroxide, the faster and more severe this burning affect to the gingival and soft tissue. This safety issue has been a barrier and a challenge to the development of tooth whitening techniques that employ higher (e.g., greater than 3%) concentrations of hydrogen peroxide.

Besides the tooth whitening effects, hydrogen peroxide has also been used from years as a disinfectant. However, because hydrogen peroxide is considered to be a primary irritant, exposure guidelines are narrow, e.g., the OSHA permissible exposure limit is 1 ppm (eight hour time weighted average) and the NIOSH "immediately dangerous to life and health" limit is 75 ppm. See e.g., http://en.wikipedia.org/wiki/Disinfectant; and "CDC—Immediately Dangerous to Life or Health Concentrations (IDLH): Chemical Listing and Documentation of Revised IDLH Values—NIOSH Publications and Products". Cdc.gov. 2009 Jul. 31. Retrieved 2012 Nov. 10. Consequently, bottles of hydrogen peroxide solution commercially available to the general public at pharmacies are 3% solutions. Because of the dangers associated with concentrated hydrogen peroxide are well known, the possible benefits of treating the skin or tissues within the oral cavity with higher concentrations of hydrogen peroxide (e.g., above about 3%) remain to be explored.

SUMMARY

A kit for one-step teeth whitening is disclosed in accordance with one embodiment. The kit comprises a container comprising a mouthpiece, a spray nozzle and an actuator; and an aqueous solution within the container, the solution comprising greater than or equal to 6% hydrogen peroxide by weight; wherein upon actuation, the mouthpiece and spray nozzle are configured to deliver onto the surface of the teeth and adjacent soft tissue an aerosol comprising the solution, such that the hydrogen peroxide causes teeth whitening, without discomfort or damage to soft tissues in the mouth. In a variation, the kit further includes instructions for using the one-step kit.

In some embodiments of the one-step kit, the solution comprises greater than or equal to 12.5% hydrogen peroxide by weight. Alternatively, the solution may comprise greater than or equal to 35% hydrogen peroxide by weight. In other embodiments, the solution comprises between about 6% and 75% hydrogen peroxide by weight.

In some embodiments of the one-step kit, the solution further comprises one or more additional ingredients. The additional ingredients may be selected from flavorings and surfactants.

In one embodiment of the one-step kit, the actuator is a finger-operable pump.

A kit for two-step teeth whitening and oral hygiene is disclosed in accordance with another embodiment. The kit comprises: a container comprising a mouthpiece, a spray nozzle and an actuator; an aqueous solution within the container, the solution comprising greater than or equal to 6% hydrogen peroxide by weight, wherein upon actuation, the mouthpiece and nozzle are configured to deliver onto the surface of the teeth and adjacent soft tissue an aerosol comprising the solution, such that the hydrogen peroxide causes teeth whitening, without discomfort or damage to soft tissues in the mouth; and a powder formulation comprising xylitol and a core composition comprising a carbon dioxide source, an adsorbent composition, and an acid, wherein the xylitol is present in an excess of at least 3 parts xylitol to 1 part core composition. In a variation, the kit further includes instructions for using the two-step kit.

In some embodiments, the carbon dioxide source in the core composition is selected from lithium carbonate, lithium bicarbonate, sodium carbonate, sodium bicarbonate, potassium carbonate, potassium bicarbonate, calcium carbonate, magnesium carbonate, ammonium carbonate and ammonium bicarbonate, and combinations thereof. In one embodiment, the carbon dioxide source in the core composition is sodium bicarbonate.

In some embodiments, the adsorbent composition in the core composition is a metal oxide or salts thereof. In some embodiments, the metal oxide is selected from silicon dioxide (silica), aluminum oxide (alumin), aluminosilicate and zirconium silicate (zircon), and salts and combinations thereof. In one embodiment, the adsorbent in the core composition is silicon dioxide (silica).

In some embodiments, the acid in the core composition is selected from citric acid, tartaric acid, fumaric acid and malic acid, and combinations thereof. In one embodiment, the acid in the core composition is citric acid.

In some embodiments of the two-step kit, the powder formulation is in the form of an effervescent powder or an effervescent tablet. In some embodiments, the powder formulation further comprises a remineralization agent. In one embodiment, the remineralization agent is a nanomaterial comprising hydroxyappetite crystals on nanoparticles. In some embodiments, the powder formulation further comprises additional ingredients. At least some of the additional ingredients may comprise flavoring agents.

A powder formulation for promoting oral hygiene is disclosed in accordance with another embodiment. The powder formulation comprises xylitol and a core composition comprising a carbon dioxide source, an adsorbent composition, and an acid, wherein the xylitol is present in an excess of at least 3 parts xylitol to 1 part core composition.

A method for whitening teeth is disclosed in accordance with one embodiment. The method comprises: administering directly onto the surface of teeth an aerosol spray comprising an aqueous solution comprising greater than or equal to 6% hydrogen peroxide by weight.

In a variation, the method further comprises swallowing or expectorating the hydrogen peroxide solution.

In another variation, the method further comprises administering into the oral cavity after the aerosol spray a powder formulation comprising xylitol and a core composition comprising a carbon dioxide source, an adsorbent composition, and an acid, wherein the xylitol is present in an excess of at least 3 parts xylitol to 1 part core composition. The powder formulation may be administered after the aerosol spray. Alternatively, the powder formulation may be administered after swallowing or expectorating the hydrogen peroxide solution. In one particular embodiment, the powder formulation is administered not more than 60 minutes after the aerosol spray.

The two steps of administering the aerosol spray and administering the powder formulation may be used to treat early stages of periodontal diseases, as a pre-treatment for gum surgery, as a pre-treatment for dental prophylaxis, as a post-treatment for dental prophylaxis, and/or to reduce bacterial count in the oral cavity.

A method of treatment is disclosed in accordance with another embodiment. The method comprises: administering into the oral cavity a powder formulation comprising xylitol and a core composition comprising a carbon dioxide source, an adsorbent composition, and an acid, wherein the xylitol is present in an excess of at least 3 parts xylitol to 1 part core composition.

The step of administering the powder formulation is used to treat early stages of periodontal diseases, as a pre-treatment for gum surgery, as a pre-treatment for dental prophylaxis, as a post-treatment for dental prophylaxis, and/or to reduce bacterial count in the oral cavity.

BRIEF DESCRIPTION OF THE DRAWINGS

FIGS. 5A, 5B, 5C, 5D and 5E are views of another mouthpiece.

FIG. 7 is a graph showing the sustenance of the bicarbonate ion in a salivary mixture.

DETAILED DESCRIPTION

Figure 1A:
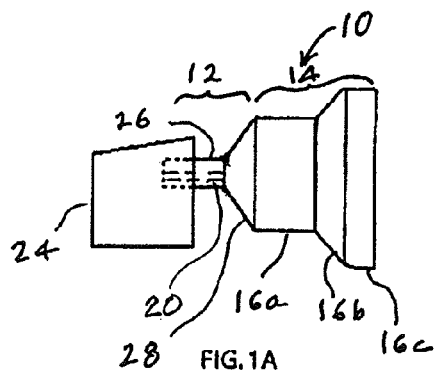
FIGS. 1A, 1B, 1C and 1D are views of a container with mouthpiece.
Figure 1B:
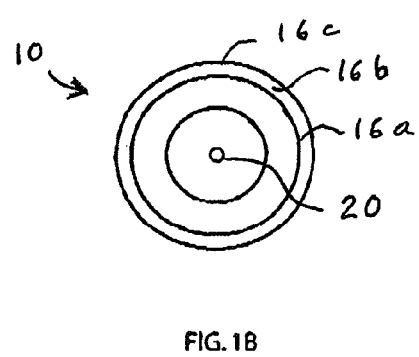
Figure 1C:
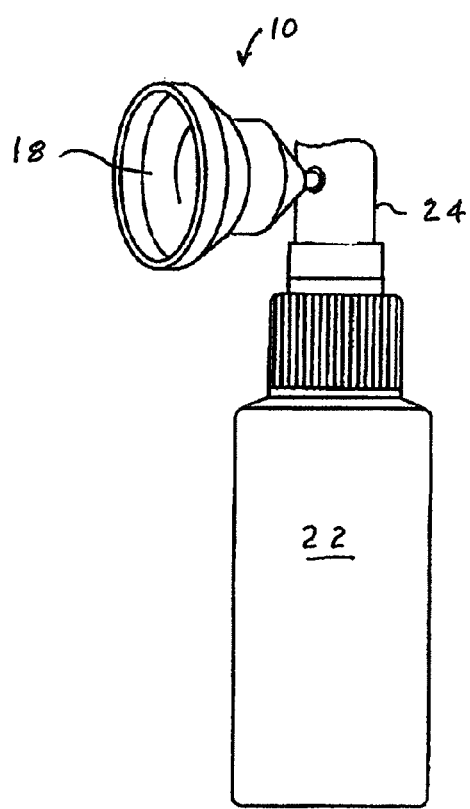
Figure 1D:
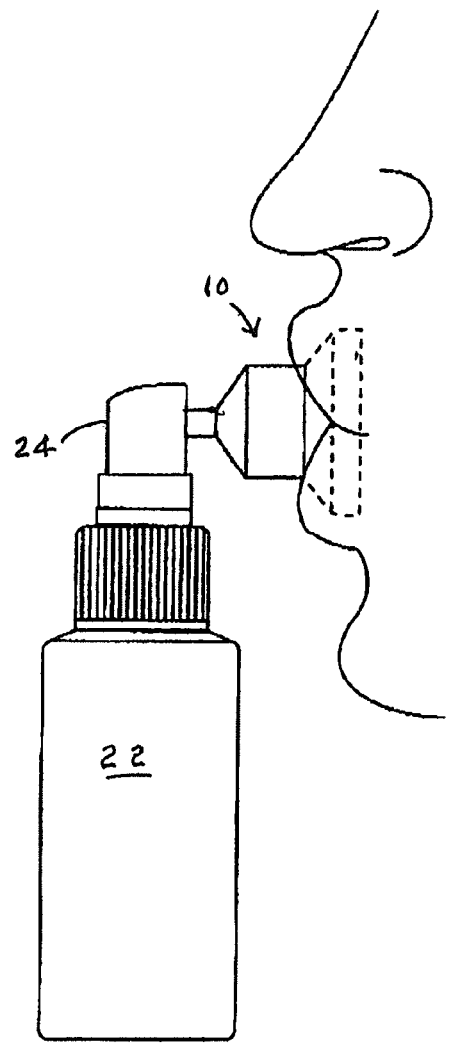
Figure 2A:
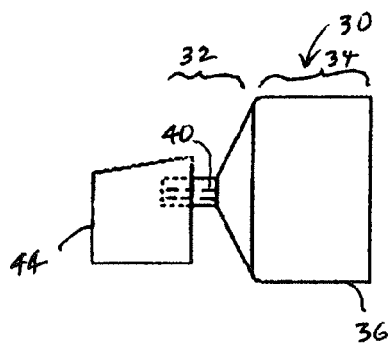
FIGS. 2A, 2B, 2C and 2D are views of another mouthpiece
Figure 2B:
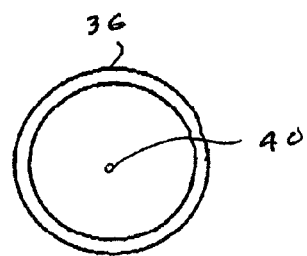
Figure 2C:
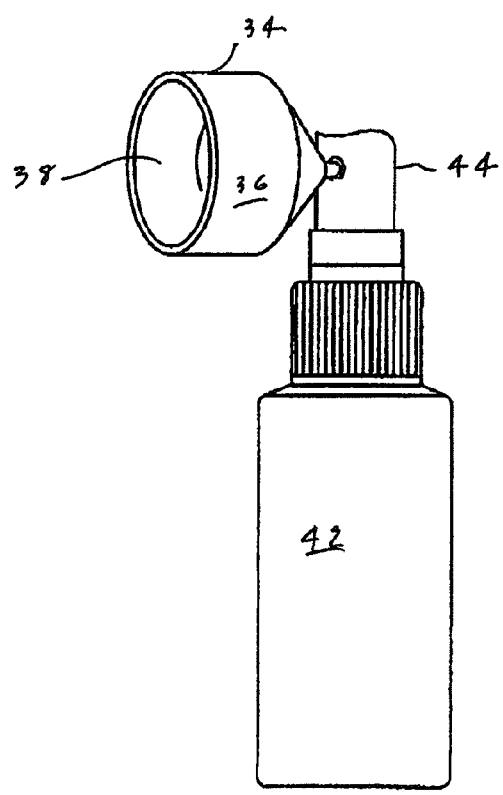
Figure 2D:
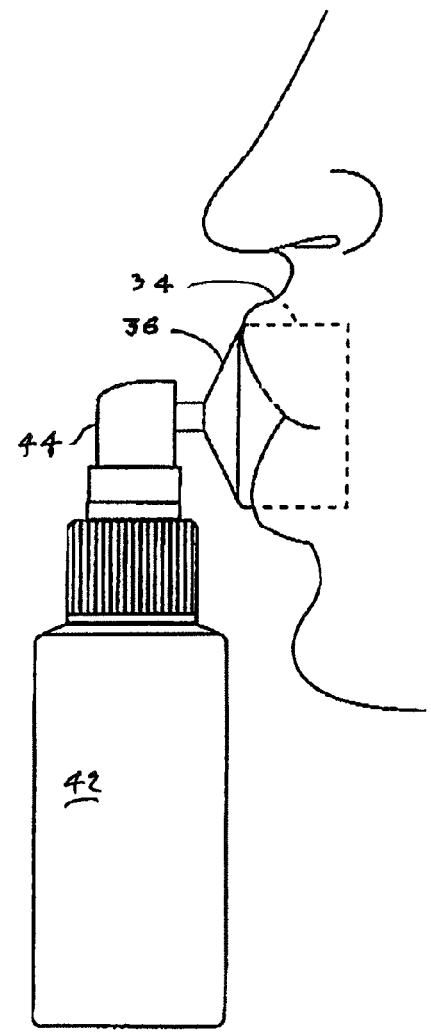
Figure 3A:
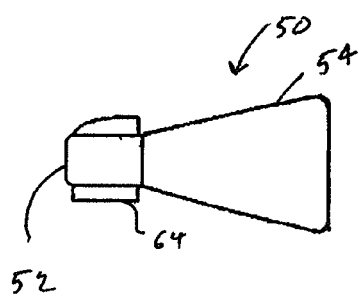
FIGS. 3A, 3B, 3C, 3D and 3E are views of another mouthpiece
Figure 3B:
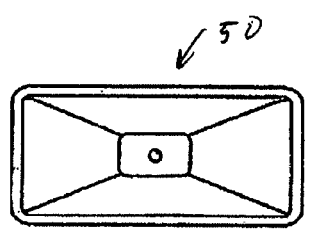
Figure 3C:
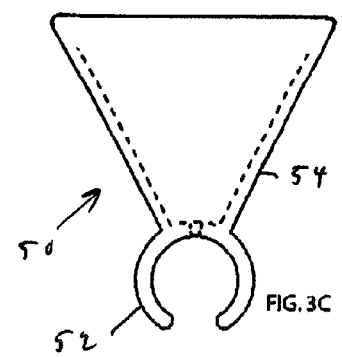
Figure 3D:
Figure 3E:
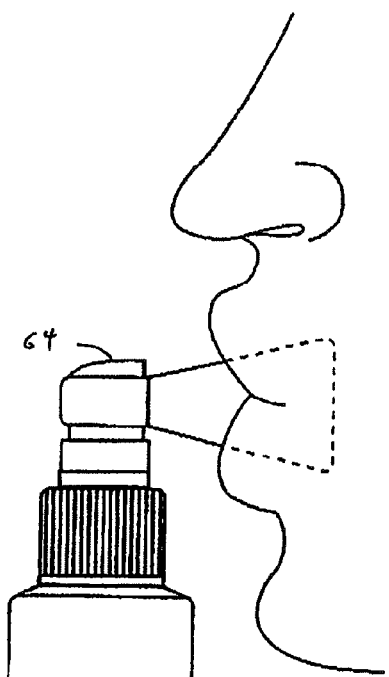

Hydrogen peroxide has been used for years as a tooth whitener as well as a disinfectant. Over nearly a century, empirical testing has led to the conventional wisdom that hydrogen peroxide must be used at very low concentrations when contacting skin or mucosal tissues of animals. Indeed, there are laws and regulations in place to limit the sale of concentrated hydrogen peroxide to the general public. Typically, a 3% solution is considered safe—this is the form of hydrogen peroxide generally available to the public. Unfortunately, optimal tooth whitening and disinfectant properties of hydrogen peroxide are observed only at higher concentrations of hydrogen peroxide. While some solutions have been developed in the tooth whitening area, e.g., gel formulations or strips that provide slow release, or physical dams that prevent contact of high concentration hydrogen peroxide with gums and soft tissues in the oral cavity, none of these solutions yield maximal efficacy or consumer convenience. Disclosed herein are compositions and methods that take advantage of the heretofore unknown and surprising properties of high concentration (well above 3%) hydrogen peroxide when provided in an aerosolized form.

Tooth Whitening with Aerosolized Hydrogen Peroxide

Tooth whitening using aqueous, or ethereal solutions of extremely high concentration of hydrogen peroxide (25%-35%) are well established as the fastest and most permanent methods available, today. These treatments require professional guidance and care, and are typically carried out in the dental office by a highly trained dental professional. This method is referred to as vital bleaching, and is tedious, and dangerous if carried out without professional application. Vital bleaching requires physical protection of the gums from exposure to the highly concentrated bleach solution (gingival dam). The dental professional custom fits a plastic damming structure around the gingiva, also places a retractor inside the lips and then lifts the lips away from the front surfaces of the teeth to keep the inside of the lips and other oral soft tissue from contact with the powerful bleaching solution. These techniques are necessary to avoid the inevitable and immediate sharp pain and burning sensation that would take place immediately without such, and also to minimize damage to the gingiva and oral soft tissue due to the aggressive burning of the tissue from the concentrated hydrogen peroxide bleach. This method has been shown to be the most effective tooth whitening method available, but is limited in its usefulness, since it must be performed by the dental professional, and requires 1-6 visits to the dental office and takes at least an hour to perform each visit, and cost ranges between $500 to $3,000 USD; rather expensive and time consuming for the average person. A popular in-clinic vital bleaching method uses heat or UV light to activate the peroxide bleach in situ and is named Zoom Whitening.

A strong desire for do-it-yourself tooth whitening methods and products exists, as evidenced by the current market popularity of many do-it-yourself products commercially available. One such product is comprised of a viscous bleaching gel contained in a professional or non-professionally fitted plastic tray, designed to provide a reservoir for the bleach as a viscous gel, and to encase the upper or lower teeth where whitening is desired. The method has the bleach in a tray to minimize exposure to the sensitive tissue. The gel form of the hydrogen peroxide bleach has the advantage in minimizing discomfort to the user, in that the exposure of the bleach to the enamel is slow due to the gel's high viscosity, and even if a leak occurs and the bleach touches the sensitive tissue, the concentration of the bleach is much lower than those employed by the vital bleaching technique. Some of the popular tray method products include Den Mat Night White, and Opalescence (3.5-8% bleach [10%-25% urea hydrogen peroxide, respectively]). The method has the user apply the tray daily for periods ranging from 20 min to 12 hours for at least 10-14 sequential days. This method has the advantage to the vital bleaching method because it can be done in the privacy of one's home and achieves reasonably good results. It uses gelled forms of bleaching solutions that are quite viscous, and more concentrated that what is available OTC for safe oral rinse application (1.5%-3% hydrogen peroxide), but much less concentrated than the vital bleaching method (25%-35% hydrogen peroxide). Typically, the concentrations of peroxide bleach in these tray method gels are on the order of 3.5% peroxide to about 8% peroxide, where urea is used as a stabilizing agent. A 10%-25% urea hydrogen peroxide gel provides for 3.5%-10% hydrogen peroxide activity, respectively. The tray method suffers because it is uncomfortable, time consuming and messy to use. Since the tray is fashioned to have the gel exposed to the front surfaces of the teeth, it only results in the bleaching of the front portions of the teeth encased in the tray. The method does not bleach teeth that are not encased by the tray, nor does it bleach the back and side areas of such teeth. In summary, the tray method suffers from the requirements that: (a) it must be performed multiple times (10-60); (b) it must stay on for an extended period of time each use (20 min-12 hr); (c) it is accompanied with some discomfort due to poor fitting trays, and dehydration of the teeth, and is messy to use, and; (d) in most cases still requires an initial visit to the dental professional to create the tray and provide instructions, and; is costly, the price ranging from 300-600 USD, and; (e) it does not provide the ability to bleach the inside portions, and hard to reach side portions of the teeth.

A similar technology is the "strip matrix" in which the hydrogen peroxide bleach solution of 6% (Crest Whitestrips, Procter and Gamble) or 14% (Crest Whitestrips Supreme, Procter and Gamble) is a thin layer on a plastic strip that is applied directly to the surface of the teeth. Bleaching of the front portions of the teeth takes place slowly over time by having the hydrogen peroxide slowly leak out of the strip matrix directly onto the surface of these teeth. The strip matrix minimizes exposure of the bleach to the sensitive tissue, since it does not touch the soft tissue and gingival tissue. Typically, the treatment requires the user to keep the strip on the teeth for about 20 minutes, repeating this procedure once a day for at least 5-14 days to see significant results. The technique has been reported as less uncomfortable than the "tray method", with similar tooth whitening results. Significant disadvantages are the length of time needed to get the desired whitening, the requirement for multiple uses, and the need for privacy during usage, since the wearing the strips in public has social disadvantages and are, in general, inconvenient, and also the inability to bleach the areas in between the teeth, and the back portions of the teeth.

Tooth whitening toothpaste compositions are also commercially available, but most of these use abrasion rather than bleaching agents for the tooth whitening action. Those tooth whitening toothpaste preparations that do include bleaching agents have the bleach at very low concentrations. The effectiveness of tooth whitening toothpaste products are, at best, none to moderate.

Oral rinse solutions have been commercially sold as tooth whitening and breath freshening mouthwash products (one current commercial example is Crest Tooth Whitening Oral Rinse), and similar solutions have been utilized as a breath freshening and tooth whitening spray (U.S. Pat. No. 5,611,690). These oral rinse methods are limited in the amount of the bleach that can be utilized in the bleaching solution, which in these cases are also breath freshening solutions, since oral rinses having greater than 3% are known to be dangerous to the user if left in the mouth for much longer than 15 seconds. In Europe and Canada, it is illegal to dispense tooth whitener or breath freshening products having concentrations of hydrogen peroxide greater than 1.5%, and 3% respectively. Effective tooth bleaching action for these types of products would, in concept, require much longer exposure times than is practically possible for these lower concentrated solutions of bleach. Since the decomposition of peroxide in the oral cavity would most likely occur before any appreciable tooth whitening, and the corresponding pain and possibly injury to the user most likely would be a result of these long durations of exposure, these oral rinse tooth whitening methods are severely hampered.

The rationale for formulating these breath-freshening bleaching solutions provided by example in the spray taught by Summers et al. was, most likely, based on the understanding of the tooth whitening and oral hygiene art. That is, since no evidence had been provided by the teachings of the tooth-whitening and oral care art to suggest otherwise, hydrogen peroxide solutions having concentrations greater than 3% were considered as dangerous agents for use as oral rinses in the human mouth and, therefore, were considered dangerous for use as an oral spray. As a direct result of this wisdom, the obvious concentration of hydrogen peroxide for employment in the teachings of Summers et al. was those of accepted oral compatibility as oral rinse solutions, i.e., less than 3% hydrogen peroxide.

The need exists for a tooth whitener that is convenient, safe and effective, without the disadvantages of the prior methods, which are the following: (a) the high cost and inconvenience of professional application of highly concentrated solutions of bleaching agent (vital bleaching method) to achieve the optimal tooth whitening results; (b) the high probability of serious injury resulting from non-professional application of the higher concentrations of hydrogen peroxide, including the vital bleaching method and spray method of Summers et al.; (c) the inconvenience that the user must endure with the spray method taught by Summers et al. due to the high frequency of usage required for, at best, poor to moderate tooth whitening results; (d) the long duration of contact with the bleaching agent required by the tray and strip methods and the corresponding inconvenience engendered; (e) the increased discomfort effected to gingiva and soft tissue of the oral cavity by the vital bleaching, tray and strip methods; (f) the inconvenience of multiple uses or socially unacceptable paraphernalia such as a tray or strip, (g) the lack of bleaching activity on the non-front surfaces of the teeth, and; (h) possible de-mineralization of the surfaces of the teeth may occur after exposure to bleaching agent, and or acidic conditions.

Periodontal diseases, including gingivitis, are a major contributor to ill health in the United States and worldwide. Periodontal diseases if left unchecked can cause the loss of teeth, and most likely will lead to an array of systemic diseases and maladies, and many of these diseases, unfortunately, will ultimately result in serious debilitation or in many cases, death. Preventive treatments for periodontal diseases include antibacterial topical solutions or oral rinses, in addition to a well-practiced regimen of good oral hygiene comprised of tooth brushing and flossing. Remedial treatments for periodontal diseases include scaling and root-planning procedures carried out in the clinic by the periodontist, and in severe cases, removal of the diseased tooth body. Another well-accepted method of prevention and remedial treatment for gingivitis (early stages of periodontal disease) is that described by Dr. Keyes (known as the Keyes technique), where a mixture of baking soda and hydrogen peroxide are applied directly to the teeth (hard tissue) and gums (soft tissue), usually by a tooth brushing methodology. The results obtained from such method for the prevention and remediation of early stage periodontal disease is moderate to significant, however, this Keys methodology suffers from being rather inconvenient and fowl tasting.

Halitosis (oral malodor) is another common oral ailment affecting millions of people worldwide. The main cause of halitosis is the presence of sulfides and amino-based compounds generated as metabolic products of certain anaerobic oral bacteria. It is the sustained growth of certain oral bacteria that thrive in the pockets of the gingival that give rise to the halitosis problem. Most of these bacterial species are relevant to the incidence of gingivitis and periodontal diseases. Thus, controlling the ill-growth of certain anaerobic bacteria that thrive in the pockets of the gingiva where oxygen supplies are minimal is desirable, since such control would most likely result in an increase in health for the gingiva and a less odiferous oral cavity. This may benefit the user by aiding in the prevention of serious systemic and oral ailments, and aesthetically by providing the user with a confident and healthy smile. The reduction of such bacteria and bacterial chemical metabolic by-products such as odiferously unpleasant oral sulfides and amines, have been achieved to some degree by employing a regiment of daily usage of oral rinses including such drugs as chlorhexidine, and/or lesser active agents such as mineral spirits, zinc or copper salts. The Keyes technique has also been employed to address the reduction in halitosis causing agents. All of these techniques suffer from the inconvenience of the requirement that they are used in the home or office, which limits the number of times the user may employ these treatments throughout the day. It is the frequency of usage that gives rise to the effectiveness in many of these agents and techniques, so lack of usage gives rise to lack of significant results.

The present disclosure provides a novel tooth whitening method and apparatus that is easy, discrete and convenient to use, and is quick acting to achieve tooth whitening results that are typically obtained from methods utilizing the professional office; and markedly better than any out-of-office treatment offered in today's marketplace. It also provides for novel re-mineralizing post-treatment compositions, pre-prophy treatment compositions and protocols, chlorhexidine replacement therapies, treatment protocols and compositions for oral wound healing.

The efficacy derived from the "out-of-office" technique is afforded by providing for a safe method and apparatus for applying an increased concentration of hydrogen peroxide as an aerosol mist, directly to the surfaces of the teeth to be bleached—while being completely devoid of the safety concerns which hampered the prior art.

Specifically, some embodiments provide for an aerosol containing hydrogen peroxide of appreciable and effective concentrations (6%-75%), to be sprayed directly onto the teeth without the anticipated sensitivity to the gums and oral tissues. In addition, one embodiment relates to a spray method and apparatus therefore that avoids the potential harmful effects of having the bleaching solution contact the eyes, lips, facial tissue, and other sensitive human tissue, and garments due to misdirected spray. Also, embodiments disclosed herein overcome the need for many applications, since the disclosed compositions and methods may be used once every third day, or once a day, depending on the strength of the treatment. Also, the inconvenience of the prior art in connection with long duration times of treatment using apparatus that requires privacy, in particular the tray and strip methods, may be overcome. In one embodiment, a convenient spray method is disclosed, in which the method can be practiced without the need to hide or experience embarrassment, and is effective in less than 2 minutes.

The need for convenient oral preparations to aid in the prevention and remediation of gingivitis, periodontal diseases, and halitosis, as well as remineralization, may be addressed in certain embodiments disclosed herein by incorporation of the alternatives; that is by incorporation of modified versions related to the plaque removal and anti-plaque compositions of Arnold as described in U.S. Pat. Nos. 6,086,854, 5,965,110, and 5,804,165 (hereafter "Arnold") post tooth whitening treatments; the entire contents of which are incorporated herein by reference.

In one embodiment, there is disclosed a safe and effective tooth bleaching spray composition, comprised of certain aqueous solutions of concentrated hydrogen peroxide. The terms "whitening" and "bleaching" are used synonymously herein. The concentration of the hydrogen peroxide delivered as an aerosol spray may be between about 6% and about 75%, alternatively between 8% and 50%, and further alternatively between 12.5% and 35% by weight. These hydrogen peroxide solutions may have other additives, including flavorings and surfactants. The preferred dosage for a single aerosol spray event is an aliquot of from about 5 mg to 1000 mg, the more preferred aliquot is from about 15 mg to 750 mg, and most preferred from about 35 mg to 225 mg.

It has been observed that the smaller the droplet size in the aerosol spray, the lesser is the sensitivity. The best device to deliver the aerosol spray, therefore, is one that provides for extremely small droplet sizes. These devises are to be made from hydrogen peroxide compatible materials, such as polyethylene, polypropylene, glass, Teflon, or other materials known safe to store hydrogen peroxide, and are adaptations of spray devices, common to modern cosmetology and oral spray technology, or to compressed gas aerosol spray technology. The adaptations of the spray devices for application of aerosolized hydrogen peroxide include a specially configured mouthpiece, where the lips surround the mouthpiece and thus inhibit or block the spray solution from exiting the targeted dental areas while directing it to the target areas. Descriptions of embodiments of the spray devices are provided below and illustrated in the Figures. The mouthpiece embodiments described below with reference to the illustrations of FIGS. 1-6 are non-limiting examples. That is, other mouthpiece designs are encompassed, as long as they serve at least one or more of the purposes to: (1) protect the lips, facial tissue, nose mucosal tissue, eye tissue, other external tissues, and garments from the peroxide containing aerosol; (2) aid in the focus of the spray to the surfaces of the enamel, and; (3) inhibit, to some degree, the aerosol bleaching mixture from direct contact with inner oral surfaces of the lips. Also, the mouthpiece embodiments are shown in forms that can be applied to known dispensing containers as well as for especially made dispensing containers. The disclosed spray devices inhibit the spray from escaping from the mouthpiece, since spray forms of hydrogen peroxide solutions having concentrations between 5% and 40%, can be damaging to the eyes, and cause an immediate discomfort and burning sensation to the lips and facial skin tissues, and since they also serve to eliminate the potential problem of the spray from reaching the garments the user is wearing, where exposure to hydrogen peroxide would ruin the garment. The proper use of this embodiment is to have the lips of the user wrap around the mouthpiece device, thus inhibiting the spray from interacting with tissue and material external to the inside of the oral cavity. Such proper use also facilitates the user comfort and safety aspects by minimizing the exposure to the non-keratinized soft tissue, which includes the inner lips and inner-oral tissues, including the tongue. It also serves to help direct and focus the spray particles onto the target surfaces of the hard tissue of the enamel. The spray may be a pump aerosol spray, or an aerosol spray form having the hydrogen peroxide solution propelled by compressed inert gas, usually butane gas, and as such having a corresponding aerosol container suitable to such pressures and such a delivery system. Such gas-propelled or hand actuated pump aerosol spray delivery systems are commonplace in today's consumer market.

The apparatus of one embodiment is a mouthpiece attachment to a spray canister, the attachment being configured to attach to the spray canister to allow the canister contents to be sprayed into the mouthpiece attachment and to allow the spray to be sprayed into the user's mouth, directed to the teeth while inhibiting any escape of the spray.

One embodiment of the attachment is shown in FIGS. 1A-1D showing a spray attachment 10. The spray attachment 10 has a nozzle adapter end 12 and a spray control end 14 also referred to as a mouthpiece portion, which is configured as circular walls 16*a*, 16*b*, 16*c* defining a progressively enlarging interior volume 18. The circular walls start at a proximate end with a smaller cylindrical portion 16*a*, then to a frustum portion 16*b* and then to a final cylindrical portion 16*c* at a distal end. As will be seen this configuration helps with the sealing effect when it is placed in a user's mouth since the lips can surround the smaller portions 16*a* and 16*b* and allow the larger portion 16*c* to be proximate the teeth in order to direct the spray onto the teeth. A spray entry opening 20 at the proximate end extends through the nozzle adapter end 12 into the interior area. The spray attachment 10 is fitted to a spray bottle 22 that has a spray nozzle 24. The nozzle adapter end 12 is configured in this embodiment as an insert tube 26 and a transition frustum 28 that can be inserted into the spray nozzle 24 and sealed to ensure that the full volume of spray is ejected as a fine aerosol mist from the spray bottle 22 when it is operated, directing the aerosol spray exiting the spray nozzle 24 through the spray attachment 10 from which it is expelled at the opening of the distal end as an aerosol spray onto the target area.

FIG. 1D shows how the spray attachment 10 is inserted into the user's mouth. It will be surrounded by the user's lips in a sealing manner on the exterior of the mouthpiece portion 14 so that no spray can escape into contact with the lips, or outside the user's mouth into contact with the face, nose, eyes or clothes. Because of the configuration of the mouthpiece portion 14, the user's lips can close on the cylindrical portion 16*a*, with the frustum portion 16*b* on the interior of the lips and the cylindrical portion 16*c* directing the aerosol spray toward the teeth.

In use, with a tooth whitening solution in the spray bottle 22 the spray control end 14 is inserted into the oral cavity is shown in FIG. 1D, where the lips surround and encase the exterior of the mouthpiece portion 14, thereby inhibiting the ejection of any misdirected solution and keeping it away from the eyes, nose, facial tissue and clothes. Proper usage has the user hold the apparatus placing the distal end opening in close proximity to the teeth in a selected starting position, typically at one side of the mouth at a series of teeth, although starting at the front is also available, pump the spray nozzle 24 once, then sequentially move it laterally and repeating the sequential spray steps 2-6 times until all the teeth have been sprayed with the whitening aerosol spray solution. The diameter of the exit of cylinder 16*c* can range from about ¾ in. to about 1½ in, 1¼ in being preferred so as to fit a wide range of users.

FIGS. 2A-2D shows another configuration of a spray attachment 30 like the one shown in FIGS. 1A-1D but with a simpler configuration of the spray attachment 30. The spray attachment 30 has a nozzle adapter end 32 and a spray control end 34 also referred to as a mouthpiece portion, which is configured as a cylinder 36 so that the interior space has an axially constant volume 38. This configuration allows a sealing effect when it is placed in a user's mouth. An opening 40 extends through the nozzle adapter end 32 into the interior volume 38. The spray attachment 30 is fitted to a spray bottle 42 that has a spray nozzle 44. The nozzle adapter end 32 is configured in this embodiment as an insert tube 46 and a transition frustum 48 that can be inserted into the spray nozzle 44 and sealed to ensure that the full volume of spray is ejected as a fine aerosol mist from the spray bottle 42 when it is operated, directing the spray exiting the spray nozzle 42 through the spray attachment 30 from which the spray is expelled as an aerosol spray.

FIG. 2D shows a proper fit for the cylindrically shaped spray control end 34 into the oral cavity, where the user's lips, surround the spray control end 34, encasing its outer surface forming an substantial seal, thereby inhibiting the ejection of any misdirected whitening solution and keeping it away from the eyes, nose, facial tissue and clothes. Proper usage has the user hold the apparatus, pump the spray nozzle 24 once, then move the unit laterally starting from one side of the mouth, and repeating the spray process 2-6 times until all the teeth have been saturated with the whitening aerosol spray solution.

Another embodiment is shown in FIGS. 3A-3E showing a spray attachment 50. The spray attachment 50 has a nozzle adapter end 52 and a spray control end 54 also referred to as a mouthpiece portion which is configured as an expanding rectangular cross-section defining a progressively enlarging interior volume 58. An opening 60 extends through the nozzle adapter end 52 into the interior volume 58. The nozzle adapter end 52 has a clip-on configuration, having curved legs 56*a* and 56*b* that are sufficiently flexible to grip the spray nozzle 64 on the spray bottle 62, so that the opening 60 is aligned with the orifice of the spray nozzle 64, thereby maintaining the integrity of the spray directed into the volume 58. This embodiment can also be made so that the spray attachment 50 is integral with the spray nozzle 64, in which case the legs 56*a* and 56*b* would form a closed circle. FIG. 3E shows a proper fit into the oral cavity where the user's lips, surround the mouthpiece portion 54, encasing the outer surface, forming an airtight seal, thereby inhibiting the ejection of any misdirected whitening solution and keeping it away from the eyes, nose, facial tissue and clothes. Proper usage has the user hold the apparatus, pump the spray nozzle head 12, once, then move the hand-held spray bottle 62, laterally starting from one side of the mouth, and repeating the spray process 2-6 times until all the teeth have been saturated with the whitening aerosol spray.

Another embodiment is shown in FIG. 4. In this embodiment the attachment 70 has a nozzle adapter end 72 which has a soft plastic cover member 74 which is sufficiently flexible that when depressed from the top as at 76, it will collapse along a portion shown at 78 below the orifice of the spray nozzle 80. This will maintain an opening 82 in the nozzle adapter end 72 aligned with the exit orifice of the spray nozzle 80. The mouthpiece end of this embodiment can have any desired configuration.

Another embodiment is shown in FIGS. 5A-5E showing an integral spray nozzle 100 on a spray bottle 102. The shape of the mouthpiece end can be selected as desired, including any of the configurations described herein as well as other configurations that are made to direct the whitening aerosol spray to the user's teeth and at the same time providing a seal to the user's lips to inhibit escape of any of the spray. This spray nozzle 100 is different from those depicted in the previous description because it is assembled as an integral spray nozzle head 110 with a spray bottle 102, including the channel required to eject the whitening solution as a fine aerosol spray; although it could also be supplied to be fitted to a pre-existing spray bottle as in the previous examples. In this embodiment the mouthpiece 104 is configured as an expanding rectangular cross-section ending in concave upper and lower edges 106a and 106b adapted to follow the general curvature of the upper and lower dental areas of a typical human oral cavity. A complete hand-held spray tooth whitening device 108, is illustrated in FIG. 5D, where the spray nozzle head 100 is assembled as an integral part of typical atomizer bottle 102. A cylindrical container having a volume of 2 ml is depicted as the atomizer pump reservoir. An illustration of a proper fit for the spray control end 104 is shown in FIG. 5E, where the user's lips surround the mouthpiece portion 104, encasing its outer surface, forming an airtight seal, thereby inhibiting the ejection of any misdirected whitening solution and keeping such away from the eyes, nose, facial tissue and clothes. The curved shape of the edges 106a and 106b keep the exit of the mouthpiece portion generally equally spaced from the user's teeth by reason of the curvature. Proper usage has the user hold the apparatus pump the spray nozzle head once, then move the hand-held spray unit laterally starting from one side of the mouth, and repeating the spray process 2-6 times until all the teeth have been saturated with the whitening aerosol spray.

Another embodiment is shown in FIGS. 6A-6D showing a typical bulb pump 120 attached to a bottle 122. In this configuration any selected shape for the spray control end can be used; the one illustrated being the one shown in FIGS. 2A-2D for illustration purposes. Proper usage has the user hold the apparatus, pump the atomizer bulb 124 once to 10 times, then move it laterally starting from one side of the mouth, and repeating the spray process 2-6 times until all the teeth have been saturated with the whitening aerosol spray.

Disclosed herein is the discovery that application of concentrated hydrogen peroxide solutions (e.g., above 3%) as an aerosol spray or mist (liquid suspended as fine droplets in gaseous phase) surprisingly avoids the anticipated ill effects to the soft tissue of the oral cavity (gums), such as sensitivity and burning. It has also been discovered that application of such concentrated solutions of hydrogen peroxide as aerosols results in significantly reduced sensitivity to the pallet and tongue, and little or no serious damage to the oral inner membranes including inner lips and oral mucosa. It is noteworthy that such ill effects are the well-established toxicological properties for mouth rinses and oral preparations comprised of solutions of hydrogen peroxide having the concentrations in excess of 3%. A clinical study was undertaken to investigate the difference between the liquid mouth rinse preparations of the prior art in direct comparison to their aerosol counterparts disclosed herein. The results are described in Table 1.

TABLE 1

COMPARISON OF SOFT TISSUE SENSITIVITY TO 12.5% HYDROGEN PEROXIDE IN ORAL RINSE SOLUTION VS AEROSOL FORMS

| SUBJECT | 12.5% RINSE | 12.5% AEROSOL | CHANGE |
| --- | --- | --- | --- |
| 1 | 5 | 1 | −4 |
| 2 | 5 | 2 | −3 |
| 3 | 5 | 1 | −4 |
| 4 | 5 | 1 | −4 |
| 5 | 5 | 1 | −4 |
| 6 | 5 | 2 | −3 |
| 7 | 5 | 2 | −3 |
| 8 | 5 | 1 | −4 |
| 9 | 5 | 1 | −4 |
| 10 | 5 | 1 | −4 |
| 11 | 5 | 2 | −3 |

SCORING:
1 NONE
2 MILD IRRITATION
3 MODERATE SENSITIVITY
4 HIGH SENSITIVITY, EXPECTORATION REQUIRED BEFORE TWO MINUTES
5 CHRONIC—EXPECTORATION REQUIRED BEFORE ONE MINUTE
6 CHRONIC—EXPECTORATION WITHIN SECONDS (IMMEDIATE SERIOUS DAMAGE)

These data demonstrate that the unpleasant and potentially harmful effects of higher (12.5%) concentration hydrogen peroxide in oral rinse preparations are completely absent when the same higher concentration hydrogen peroxide is applied as an aerosol. The results of a direct comparison between an oral rinse and an aerosol at an even higher concentration of hydrogen peroxide (35%) are shown in Table 2.

TABLE 2

COMPARISON OF SOFT TISSUE SENSITIVITY TO 35% HYDROGEN PEROXIDE IN ORAL RINSE SOLUTION VS AEROSOL FORMS

| SUBJECT | 35% RINSE | 35% AEROSOL | CHANGE |
| --- | --- | --- | --- |
| 1 | 6 | 2 | −4 |
| 2 | 6 | 2 | −4 |
| 3 | 6 | 2 | −4 |
| 4 | 6 | 1 | −5 |
| 5 | 6 | 2 | −4 |
| 6 | 6 | 2 | −4 |
| 7 | 6 | 2 | −4 |
| 8 | 6 | 1 | −5 |
| 9 | 6 | 3 | −3 |
| 10 | 6 | 2 | −4 |

SCORING:
1 NONE
2 MILD IRRITATION
3 MODERATE SENSITIVITY
4 HIGH SENSITIVITY, EXPECTORATION REQUIRED BEFORE TWO MINUTES
5 CHRONIC—EXPECTORATION REQUIRED BEFORE ONE MINUTE
6 CHRONIC—EXPECTORATION WITHIN SECONDS (IMMEDIATE SERIOUS DAMAGE)

The discovery is disclosed that a convenient and safe method exists for direct application of solutions of concentrated hydrogen peroxide to the enamel including incidentally to the gingiva and other soft tissue utilizing an aerosol spray. Since the tooth whitening art for well over 100 years has believed otherwise, the results shown in Tables 1 and 2 teach for the first time that higher concentrations of hydrogen peroxide (e.g., 12.5% and 35%), previously deemed harmful when administered as a solution (oral rinse preparation), can be safely administered as an aerosol spray. As a consequence of the safe delivery of high concentration hydrogen peroxide, tooth whitening is dramatically improved (see e.g., Tables 3 and 4). In many cases, the whitening action has been demonstrated as comparable to or better than the other methods that utilize concentrated hydrogen peroxide (strip, tray gel, paint on gel), and far better than the tooth whitening rinses, tooth whitening toothpastes, and the spray forms of the prior art using low concentrations of hydrogen peroxide. Thus, the present high concentration hydrogen peroxide in an aerosol provides results as good as or better than the existing methods, but with the advantages of quick-action and convenience.

TABLE 3

TOOTH WHITENING EFFICACY OF 12.5% HYDROGEN PEROXIDE AEROSOL APPLIED TWICE DAILY FOR TWO WEEKS

| SUBJECT | CHANGE* |
|---|---|
| 1 | 3 |
| 2 | 5 |
| 3 | 7 |
| 4 | 5 |
| 5 | 7 |

*based on the Vita Shade Guide, expressed as a change in shade guide units (+Δsgu)

The results shown in Table 3 show that an aerosol tooth whitener including 12.5% hydrogen peroxide produces a readily noticeable change in tooth whitening, from 3 to 7+Δsgu.

A further study was undertaken to demonstrate the efficacy and safety of an even higher concentration of hydrogen peroxide, delivered to the surfaces of the teeth as an aerosol. The results shown in Table 4 demonstrate that an aerosol spray generated by an apparatus such as that depicted in FIGS. 6A-D with a solution of concentrated hydrogen peroxide (35%) is very effective in whitening the teeth with just a single two minute application. Proper aerosol delivery in accordance with the disclosed apparatus and methods was no accompanied with the pain, burning and soft tissue damage that would otherwise be expected with application of such a concentrated solution of hydrogen peroxide. These results are in stark contrast to what would be expected based on current knowledge of the tooth whitening art; that is that such efficacy may be achieved without harm to the patient, and without the employ of a dam to protect the gingiva and other soft tissue, and without the need for professional technician to apply the treatment.

TABLE 4

TOOTH WHITENING EFFICACY OF 35% HYDROGEN PEROXIDE AEROSOL APPLIED ONCE FOR TWO MINUTES

| SUBJECT | CHANGE* |
|---|---|
| 1 | 7 |
| 3 | 7 |
| 4 | 3 |
| 5 | 6 |
| 6 | 4 |
| 7 | 8 |
| 8 | 7 |
| 9 | 8 |
| 10 | 8 |

*based on the Vita Shade Guide, expressed as a change in shade guide units (+Δsgu)

The aerosol spray method disclosed herein delivers hydrogen peroxide to the teeth in higher dosages than were previously believed possible due to safety concerns. It has been discovered that it is this spray method that provides the aerosol chemistry that allows for the safe application of hydrogen peroxide of higher concentration to the hard tissue present in the oral cavity, without the need for a dam to protect the gingiva and other soft tissue, and without the discomfort typically encountered for other tooth whitening techniques that use high concentrations of hydrogen peroxide.

While not intending to be bound by any particular mechanism, a possible explanation for this discovery is twofold. First, the greater surface area of the small aerosol droplets in the spray, compared to the bulk liquid (as a solution or large droplet), provides a much greater exposure of highly reactive external peroxide moieties to the target tissues. This may result in a higher effective concentration of peroxide interfacing with the saliva, where enzymes decompose the peroxide into active oxygen. Thus, the tiny droplets serve to facilitate an increased rate of reaction of the reactant peroxide, as an enzyme substrate, to the bleaching (and bactericidal) product, oxygen. Second, by administering concentrated hydrogen peroxide solutions to the mouth as tiny aerosol droplets, these small droplets bind with the hard tissue (enamel) to instantly release a concentrated flash of hydrogen peroxide (or oxygen). However, to the soft tissue and non-target mucosal areas of the oral cavity, the tiny droplets get mixed with the saliva and quickly become diluted, thus forming in situ, oral solutions of hydrogen peroxide known to be of a safe concentration. This latter explanation may provide some mechanism as to why the aerosol delivery of concentrated hydrogen peroxide provides unprecedented safety compared to oral rinse compositions, and having much greater tooth bleaching concentrations, where these concentrations are at levels previously believed to be harmful for use in the human oral cavity.

Combination Therapies

In one embodiment, a two-step combination therapy for tooth whitening and improved oral hygiene is disclosed. The first step is the application of concentrated hydrogen peroxide as an aerosolized liquid (as described above). The second step, which is applied after the hydrogen peroxide treatment in some embodiments, involves administration of a solid or powdered formulation. In some embodiments, the powdered formulation may be co-administered with the hydrogen peroxide aerosol. In some embodiments, the powdered formulation may be administered about 0.1, 0.2, 0.3, 0.4, 0.5, 0.6, 0.7, 0.8, 0.9, 1.0, 1.5, 2, 2.5, 3, 3.5, 4, 4.5, 5 minutes after applying the hydrogen peroxide aerosol. In other embodiments, the powdered formulation may be administered at any time between 0 and 30 minutes after applying the hydrogen peroxide aerosol. In other embodiments, the powdered formulation may be administered at any time between 0 and 120 minutes after applying the hydrogen peroxide aerosol. In one embodiment, the closer in time the two steps occur, the better the whitening, breath freshening and oral hygienic effects.

In certain embodiments, the powdered formulation is an effervescent tablet or an effervescent powder, which can be administered directly onto the tongue. In one embodiment, the powdered formulation is a modified version of that previously disclosed, e.g., in U.S. Pat. No. 6,086,854, and co-pending application U.S. application Ser. No. 12/061, 493; which are incorporated in their entireties herein by reference.

The powdered formulation may include a core composition that may act as a pH-buffering composition, plus xylitol, or a combination of xylitol and sorbitol. The core composition may include a carbon dioxide source, a plaque adsorbent composition, and an acid source. The carbon dioxide source may be a non-aqueous, water soluble and pharmaceutically acceptable composition, for example, a carbonate (and salts thereof), a bicarbonate (and salts thereof), and mixtures thereof. Specific carbon dioxide sources include e.g., lithium carbonate, lithium bicarbonate, sodium carbonate, sodium bicarbonate, potassium carbonate, potassium bicarbonate, calcium carbonate, magnesium carbonate, ammonium carbonate, ammonium bicarbonate, or the like. The plaque adsorbent may comprise a metal oxide, for example, silicon dioxide (silica) and salts thereof, aluminum oxide (alumin) and salts thereof, aluminosilicate and salts thereof, zirconium silicate (zircon) and salts thereof, and mixtures of these adsorbent materials. The acid source may be a non-aqueous, water soluble and pharmaceutically acceptable composition, for example, an organic acid, in particular, the fruit acids. Exemplary acids include citric acid, tartaric acid, fumaric acid and malic acid. In one embodiment, the core composition comprises sodium bicarbonate, silicone dioxide and citric acid. In some embodiments, the relative amounts of these core materials may be about 50 to 90 parts sodium bicarbonate, about 10 to 90 parts silicone dioxide, and about 2 to 20 parts citric acid.

In other embodiments, the core composition comprises about 60 to 85 parts sodium bicarbonate, about 20 to 80 parts silicon dioxide, and about 3 to 15 parts citric acid. In another embodiment, the core composition comprises about 65 to 80 parts sodium bicarbonate, about 25 to 60 parts silicone dioxide, and about 4 to 10 parts citric acid. While the relative proportions of core materials are described above with reference to one particular set of compounds, the same relative proportions may be applied to any other iteration of a carbon dioxide source, an adsorbent and an acid.

Xylitol may be added as a sweetening agent. However, it has been discovered that xylitol in certain concentrations, together with the core composition, exhibits profound, and unexpected effects on efficacy of the powdered formulation (second step of the combination therapy). Xylitol added to the core composition provides for a significantly enhanced bactericidal activity against Streptococcus mutans (S. mutans), an anaerobic bacteria known to be involved in tooth decay in humans. S. mutans has also been implicated in serious systemic diseases. It was surprisingly discovered that the combination therapies and compositions disclosed herein provide unexpectedly enhanced S. mutans reduction compared to what would be expected from xylitol alone. This is due to the synergistic effect of the core composition and the xylitol. This effect most likely occurs due to three properties conveyed to the xylitol by the core chemistry. These include: (1) increased surfactant activity; (2) pH buffered in the mildly basic region; and (3) sustansivity of xylitol. In addition, the combination also was found to significantly enhanced tooth remineralization.

In order to achieve any appreciable enhancement to the bactericidal activity of xylitol, it was discovered that xylitol is desirably present in the powdered formulation at concentrations in an excess of that previously taught. For example, in U.S. Pat. No. 6,086,854, a powdered composition similar to that described herein is disclosed as a prophylactic rinse for improved oral hygiene. The ratio of xylitol to core composition disclosed varied from 0.1666 parts xylitol to 1 part core composition up to a maximum of 2.333 parts xylitol to 1 part core composition. In accordance with certain embodiments disclosed herein, the ratio of xylitol to the core composition is increased from between about 3-20 parts xylitol to 1 part core composition. Alternatively, the ratio of xylitol to the core composition may be between about 5-15 parts xylitol to 1 part core composition. In other advantageous embodiments, the ratio of xylitol to the core composition may be between about 7-12 parts xylitol to 1 part core composition. In one particular embodiment, the ratio of xylitol to core composition is 4 parts xylitol to 1 part core composition.

Besides the use of higher concentrations of xylitol compared to prior art teachings, it has never been suggested or expected that a solid or powdered formulation (such as that disclosed herein) would exhibits synergistic effects with hydrogen peroxide aerosol (administered just prior to the powdered formulation).

The principal active ingredients in the core composition ($CO_2$ source, adsorbent, acid) act together with xylitol to reduce surface tension. The surface activity of the core composition may be due to the reduction in surface tension of the salivary matrix. More particularly, this surface tension reduction may be due to: (a) the silicon dioxide polymeric hydrogen bonding and hydrophobic effects thus exerted on the surface of the salivary matrix, thus causing for a weaker overall hydrogen bonding internal and on the surface of the salivary matrix; (b) the slightly basic pH due to the sodium bicarbonate as well as an overall reduction in the intermolecular water hydrogen bonding potential of the salivary matrix. The surface active effects of core ingredients appear to complement and enhance any surface active effects of xylitol, and since the intercellular attachment of bacteria to each other as well as the surfaces of the soft and hard tissues as well as the dental plaque surfaces are important for the vitality of the *Strep mutans*, reducing the amount and strength of the many types of chemical bonding attachment enhances the anti-caries activity.

A number of reports have been published that describe the bacteriostatic activity of xylitol on *Strep mutans* (the strain of bacteria that have been shown to be the main cause of dental caries) and its relationship to the observed effects (for example, see Wåler S M[1], Rølla G; *Nor Tannlaegeforen Tid.* 1990 March; 100(4):140-3). Here, synergy between the xylitol and core composition may provide for an unobvious enhancement of the bacteriostatic effects observed. This may be due to the extracellular pH as well as the above-described enhanced surface activity. The consequence of the pH buffering as well as the enhanced reduction of extracellular and cellular surface tension may allow for a higher intracellular concentration of xylitol, and thus a more pronounced anti-caries effect due to increased kinetics of the specific enzymatic mechanism comprising the bacteriostatic biochemistry of xylitol.

The composition is prepared such that upon usage, it causes the salivary pH to remain in the basic range, and that the pH is sustained in the basic range at least 10 minutes after usage. More particularly, it has been observed that pH increases to above pH 8 within 1 minute after administration of the powdered formulation. The pH remains above pH 7.4 for at least about 10 minutes, and then gradually declines to a normal neutral pH of about 7 within 60 minutes. The pH buffering effect is illustrated in FIG. 7.

Sustansivity of the xylitol also takes place as a result of combining xylitol with the core compositions disclosed. This may be due to the binding of the xylitol to the silica particles present in the core composition. FIG. 7 shows that the pH of the saliva remains in the mildly basic region for up to an hour after using an effervescent oral powder as described herein. This observation suggests that the xylitol is also sustained in the oral cavity after consumption. Since the drug activity of xylitol is directly related to the amount of xylitol present in the oral cavity, which may reflect the amount of xylitol inside bacterial cells, having an appreciable amount of xylitol remaining in the oral cavity after consumption provides for increase drug activity. In addition, the user is provided with an enhanced cosmetic effect, since a sweet and soothing mouth feel and aftertaste that last for many minutes gives rise to a highly satisfied user of this novel dentifrice.

In addition to the unexpected and advantageous effects of enhanced surfactant activity, pH buffering in the mildly basic region, and enhanced sustansivity, it has also been discovered that the powdered formulation also facilitates remineralization of the teeth. This allows the teeth to accommodate continued peroxide bleaching to realize optimum white color without causing harm to the hard tissue of the teeth (enamel). Remineralization may be enhanced by incorporation of one or more additional remineralizing agents. One useful remineralizing agent is a nanomaterial comprising hydroxyappetite crystals on nanoparticles. A variety of nano-hydroxyappetite formulations, are commercially available, e.g., Nano Medical Hydroxyapatite, from Sangi Company Ltd. (Japan). The amount of remineralizing agent may vary from about 0.001% to about 20% by weight, and more particularly, from about 0.1% to about 5% by weight.

Since demineralization takes place every time the ingestion of acidic foods and beverages takes place, the powder oral rinse acts to safely and immediately remedy the acidic pH by causing an adjustment to a safer, higher or neutral pH. Also the powder formulation (without any additional remineralization agent) can deliver calcium ions to the enamel, wherein calcium may integrate into the surfaces of the teeth with efficacy, thus helping to restore the teeth to their original strength.

In some embodiments, the post-treatment powder formulation may be administered alone in between the normal combination treatments (i.e., without the hydrogen peroxide aerosol-first step), for example, after the teeth have reached their optimum white color, to remove stain-causing agents. Furthermore, use of the powdered formulation (alone) aids in the control of oral pH, as well as the levels of plaque and food debris present in the oral cavity, and aid in the control and reduction of growth of harmful bacteria that implicated in periodontal diseases and halitosis, as well as systemic diseases related to these oral bacterial. It has also been found that use of the powder formulation (with or without the hydrogen peroxide first step) aids in the removal of bio-film (comprising organic and inorganic materials that accumulate in the form of dental plaque) from the enamel and gingiva. Further, as mentioned above, the powder formulation aids in remineralization of the teeth (with or without another remineralization agent). Dosing of the powdered formulation alone is at least once a day, and may be many times, for example, after eating.

The enhancement to the spray tooth whitening technique may be due to a chemical catalysis of the bleaching reaction, which aids the decomposition of hydrogen peroxide to the active bleaching oxygen moieties. This is referred to as "quenching" the bleaching reaction; that is, immediately after expelling the salivary peroxide solution resulting from application of the hydrogen peroxide aerosol, the post-treatment powder (or tablet) oral rinse effects a complete decomposition of any remaining peroxide, and thus enhances the whitening properties and minimizes any negative effects on enamel demineralization.

As mentioned above, use of an oral rinse comprising the powdered formulation is not limited to the two-step therapy employing the hydrogen peroxide spray methods disclosed herein. Indeed, the powder oral rinse with or without any added re-mineralizing agent, can be used advantageously as a post-treatment for other tooth whitening processes that utilize hydrogen peroxide. For example, utilization of the post-treatment powder oral rinse after use of a gel-tray teeth whitener would enhance tooth whitening.

Cosmetically, it has been observed that a significant synergistic enhancement takes place as a result of employment of the two-step therapy. Such synergy is evidenced by the observations described in Example (V) and the data presented in FIG. 8.

As discussed above, enhanced tooth whitening efficacy in comparison to using the aerosol spray tooth whitening treatment alone, may be due to: (1) quenching of the peroxide-enamel bleaching reaction; buffering, in the slightly basic range of the inner oral cavity, thus providing for a "soothing" mouth-feel effect, and; (3) the sustained presence of inorganic residues that aid in remineralization of the teeth.

EXAMPLES

Example I

One-Step Teeth Whitening with Aerosolized 35% Hydrogen Peroxide

| INGREDIENT | AMOUNT |
|---|---|
| Hydrogen Peroxide solution (ca 35%) FMC | 1000 grams |

Figure 4:
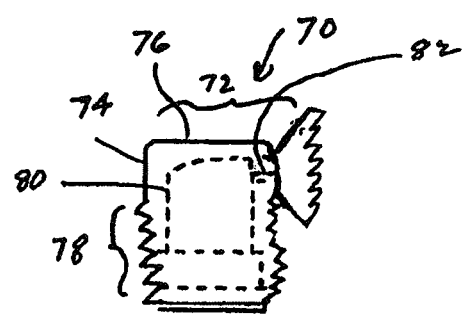
FIG. 4 is a partial view of a mouthpiece fitted to a spray device
Figure 6A:
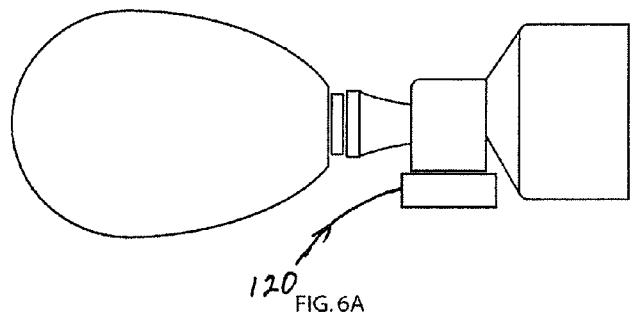
FIGS. 6A, 6B, 6C and 6D are views of another mouthpiece
Figure 6B:
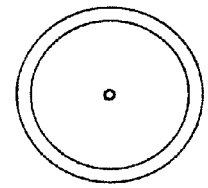
Figure 6C:
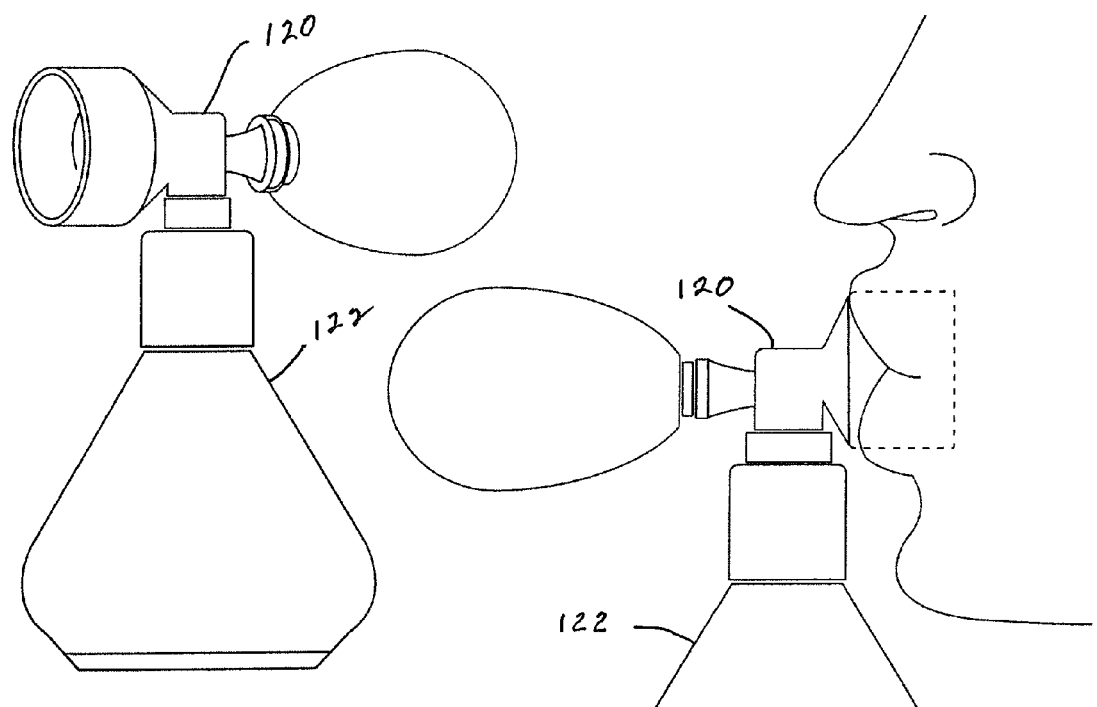
Figure 6D:
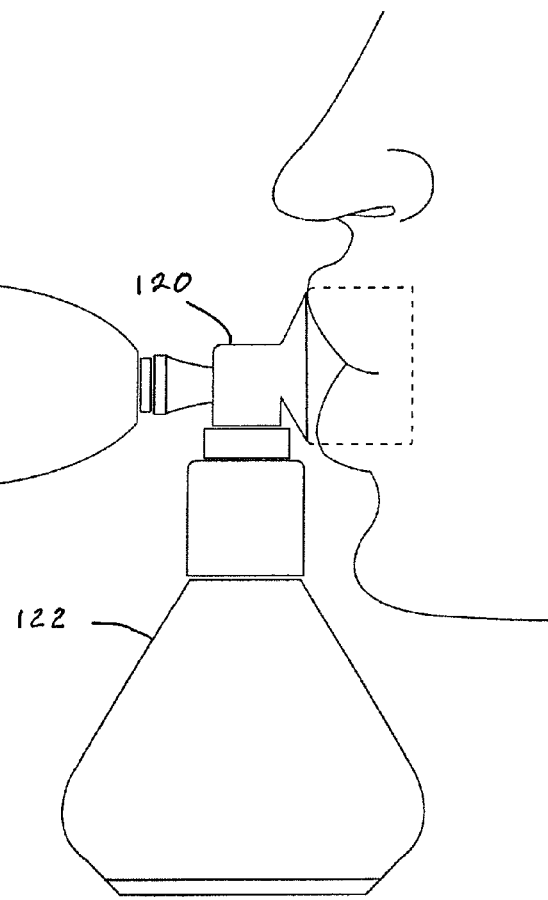

A 15 ml metal container or canister having the inside portion of the canister lined with polyethylene film was charged with 5 mL of 35% hydrogen peroxide (FMC), and then the mouthpiece-sprayhead assembly was put in place, similar to that shown in FIG. 4. The resulting fully charged spray apparatus was held with one hand, placing the unit juxtaposed to the lips such that the mouthpiece was lodged in between the lips and sealed by the lips around the mouthpiece portion of the apparatus, and with the front part of the upper teeth touching the edge of the mouthpiece, as shown in FIG. 1. Then, the spray-pump button was depressed by forefinger action and resulted in delivery of about 150 mg of a fine mist spray directly onto the surface of the teeth without regard to other surfaces in the mouth (i.e., the gingival were not protected). This application process where the forefinger depressed the pump button to actuate the spray onto the surfaces of the hard and soft tissues of the oral cavity was repeated 2 more times within a 5 seconds total applications time. A slight tingling sensation was reported, but no pain or burning or any injury was observed, or reported. After the lips were sealed, a bountiful effervescence took place and in concert with this effervescence, the subject gently swirled the salivary mixture throughout the oral cavity for about 2 minutes, then expectorated.

The subject was measured for degree of whitening using the Vita Shade Guide. A value of 4 shades+Δsgu was determined for the degree of whitening value for this single use dose. The subject was pleased with the result, and impressed with the short period of time and ease of use, however the taste and mouth feel were reported to have a slight metallic taste residue that appeared to disappear over the course of the subsequent hour.

Example II

One-Step Teeth Whitening with Aerosolized 50% Hydrogen Peroxide

| INGREDIENT | AMOUNT |
|---|---|
| Hydrogen Peroxide solution (ca 50%) FMC | 100 grams |

A 35 ml metal canister having the inside portion of the canister lined with polyethylene film was charged with 25 mL of 50% hydrogen peroxide (FMC), and then the mouthpiece-sprayhead assembly was put in place, similar to that shown in FIG. 4. The resulting fully charged spray apparatus was held with one hand, placing the unit juxtaposed to the lips such that the mouthpiece was lodged in between the lips and sealed by the lips around the mouthpiece portion of the apparatus, and with the front part of the upper teeth touching the edge of the mouthpiece, as shown in FIG. 1. Then, the spray-pump button was depressed by forefinger action and resulted in delivery of about 150 mg of a fine mist spray directly onto the surface of the teeth without regard to other surfaces in the mouth (i.e., the gingival were not protected). This application process where the forefinger depressed the pump button to actuate the spray onto the surfaces of the hard and soft tissues of the oral cavity was repeated 2 more times within a 5 seconds total applications time. A slight tingling sensation was reported, but no pain or burning or any injury was observed, or reported. After the lips were sealed, a bountiful effervescence took place and in concert with this effervescence, the subject gently swirled the salivary mixture throughout the oral cavity for about 2 minutes, then expectorated.

The subject was measured for degree of whitening using the Vita Shade Guide. A value of 8 shades+Δsgu was determined for the degree of whitening value for this single use dose. Although the subject was very pleased with the whitening result and the short period of time and ease of use, the taste and mouth feel were reported to exhibit a strongly metallic taste that disappeared over the course of the subsequent two hours.

Example III

Two-Step Teeth Whitening and Oral Hygiene Treatment with a First Step Comprising Application of Aerosolized 25% Hydrogen Peroxide, and a Second Step Comprising Administration of an Oral Powder Formulation Composition #1: Spray Whitener (Kit Component #1)

| INGREDIENT | AMOUNT |
|---|---|
| Hydrogen Peroxide solution (ca 25%) FMC | 82 grams |
| Deionized Purified Water | 18 grams |

An aqueous solution of 25% hydrogen peroxide was prepared by mixing 50 grams of 50% hydrogen peroxide with 50 grams deionized water. A 35 ml metal canister having the inside portion of the canister lined with polyethylene film was charged with 25 grams of this 25% hydrogen peroxide solution, and then the mouthpiece-sprayhead assembly was put in place, similar to that shown in FIG. 4.

Composition #2: Powder Oral Rinse (Kit Component #2)

| INGREDIENT | AMOUNT |
|---|---|
| Xylitol | 81 kg |
| Sorbitol | 10 kg |
| Sodium Bicarbonate | 7 kg |
| Silica (JM Huber ZEODENT 113) | 5 kg |
| Citric Acid | 1 kg |
| Menthol | 0.05 kg |
| Peppermint Flavor (anhydrous powder) | 0.005 kg |

To a dry ribbon blender was added one-half the amount of Xylitol, then the other ingredients were added in bulk, and the blender run at medium rate for less than 5 minutes, and then the remainder of the Xylitol was added and the resulting mixture was blended at medium rate for about 10-20 minutes. The resulting white powder was put into a polyethylene lined 55 gallon drum, purged and sealed under nitrogen. The powder was stable for over one year.

"Kit" Teeth Whitening Protocol

The spray whitening operation was performed as described in Example I. Immediately after expulsion of the salivary mixture, 2 grams of the Powder Oral Rinse (Composition #2) was poured directly onto tongue, and the lips subsequently sealed, and then the oral salivary mixture (the effervescent powder immediately dissolves to form a salivary mixture of pH>7.5) was swirled around the mouth using the tongue and cheek muscles to manipulate the oral fluid throughout the oral cavity. After about one minute, the salivary mixture was swallowed. The subject repeated this two-step procedure once a day over the course of seven consecutive days. The change in whiteness value determined using a Vita Shade Guide was greater than 5 shades. The subject commented on how clean and fresh his mouth felt, and how long lasting such a feeling endured. The dental examiner observed a stark reduction in the amount of plaque and food debris in the oral cavity subsequent to the two-step procedure. The dental examiner also noted that after one week it appeared that the subject's gums had taken on a more "pink and firm" complexion, which indicates a healthy gingiva (gums).

Example IV

One-Step Oral Hygiene Treatment Using the Oral Powder Formulation in Between Teeth Whitening Treatments This example describes an embodiment, where the Powder Oral Rinse is used in between teeth whitening treatments. In order to keep stains from accumulating on the surfaces of the teeth, and also to keep the oral cavity clean in between traditional oral cleansing operations (for example, tooth brushing and/or flossing), the Composition #2 from Example III was employed utilizing the same procedure after meals and/or snacks throughout the day, typically at least once a day. The subject noticed how white his teeth were and how the stains from morning coffee essentially disappeared after using the Powder Oral Rinse. He also stated that he felt like he had just brushed his teeth each time he used the Powder Oral Rinse.

Example V

Comparison of the Teeth Whitening Effects of the One-Step (35% Hydrogen Peroxide) Vs. The Two Step (35% Hydrogen Peroxide+Powdered Formulation)

Figure 8:
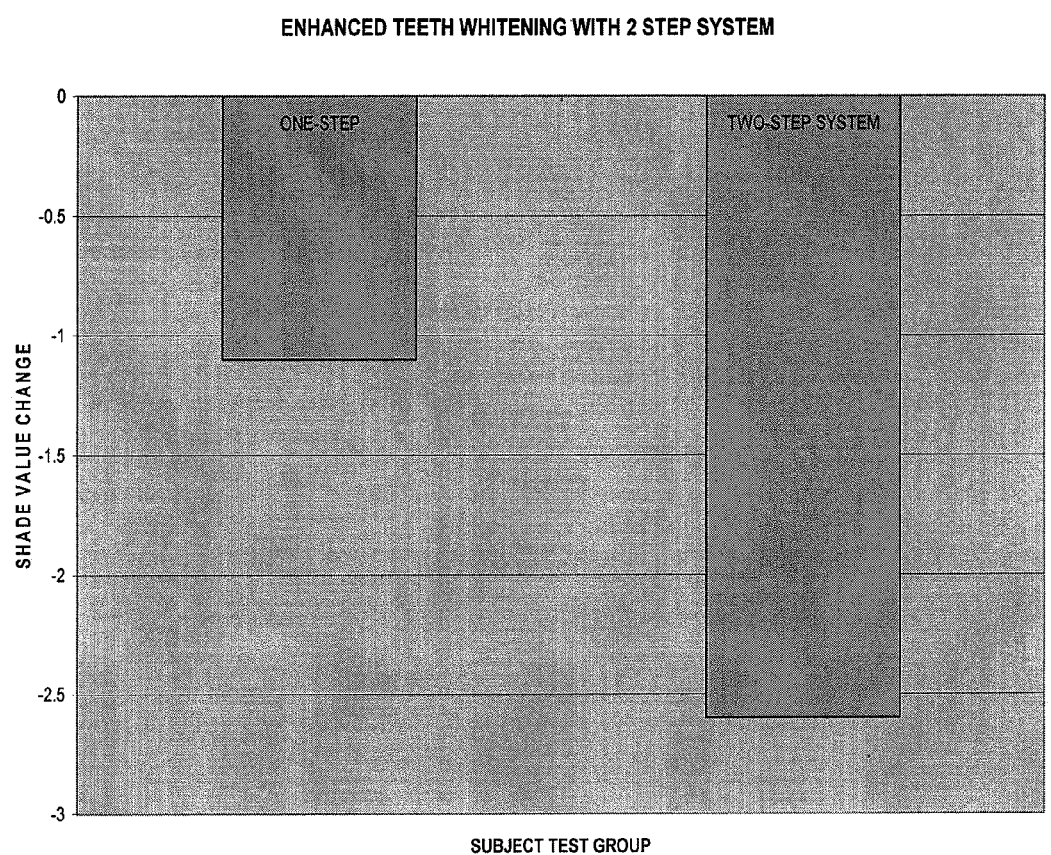
FIG. 8 shows a comparison of a one-step hydrogen peroxide spray and a two-step hydrogen peroxide spray followed by a Powder Oral Rinse on teeth whitening.

Two groups of 30 subjects each were enlisted in the clinical study under the direction of Dr. Ed McClaren, chairman of the Ceramic Department of Dentistry at the University of California at Los Angeles. The examiners were dental professionals, skilled in the art of evaluating teeth for whiteness levels, and were blind to the treatment. Two treatment compositions were provided for the double-blind study. Both groups were instructed to use the treatment with the same method (once a day). One group received a one-step treatment comprising a hand-held spray device with a container comprising a mouthpiece and nozzle, wherein the container was charged with 35% aqueous hydrogen peroxide; and the other group received a two-step treatment comprising the same hand-held spray device charged with the same 35% aqueous hydrogen peroxide, but were also given a 2 gram aliquot of Powder Oral Rinse, having the ratio of xylitol to core composition of 7 parts xylitol to 1 part core composition, applied to the tongue immediately after the hydrogen peroxide spray treatment. The results are illustrated in FIG. 8, and demonstrate that the group that used the two-step treatment not only had statistically significant teeth whitening enhancement compared to the single step spray treatment group, but also reported a high degree of oral cleansing and sanitary feeling in their mouths.

Example VI

Two-Step Combination Therapy, Wherein the Powder Formulation Administered in the Second Step Further Included a Remineralization Agent This example describes an embodiment where a remineralization composition is included. Similar to Example III, a two-step process is utilized that incorporates the first step of aerosolized hydrogen peroxide, and a second step of Powder Oral Rinse (xylitol+core composition); however in this Example, a nano-hydroxyapatite composition was included in the second step.

Composition #1: Spray Whitener (Kit Component #1)

| INGREDIENT | AMOUNT |
| --- | --- |
| Hydrogen Peroxide solution (ca 35%) FMC | 82 grams |
| Deionized Purified Water | 18 gram |

An aqueous solution of 35% hydrogen peroxide was prepared by mixing 50 grams of 50% hydrogen peroxide with 50 grams deionized water. A 35 ml metal canister having the inside portion of the canister lined with polyethylene film was charged with 25 g of this 25% hydrogen peroxide solution, and then the mouthpiece-sprayhead assembly was put in place, similar to that shown in FIG. 1.

Composition #2: Powder Oral Rinse (Kit Component #2)

| INGREDIENT | AMOUNT |
| --- | --- |
| Xylitol | 91 kg |
| Sodium Bicarbonate | 7 kg |
| Silica (JM Huber ZEODENT 113) | 5 kg |
| Citric Acid | 1 kg |
| Menthol | 0.05 kg |
| Peppermint Flavor (anhydrous powder) | 0.005 kg |
| Nano-hydroxyapatite | 0.5 kg |

To a dry ribbon blender was added one-half the amount of Xylitol, then the other ingredients were added in bulk, and the blender run at medium rate for less than 5 minutes, and then the remainder of the Xylitol was added and the resulting mixture was blended at medium rate for about 10-20 minutes. The resulting white powder was put into a polyethylene lined 55 gallon drum, purged and sealed under nitrogen. The powder was stable for over one year.

"Kit" Teeth Whitening Protocol

The spray whitening operation was performed as described in Example I. Immediately after expulsion of the salivary mixture, 2 grams of the Powder Oral Rinse (Composition #2) was poured directly onto tongue, and the lips subsequently sealed, and then the oral salivary mixture (the effervescent powder immediately dissolves to form a salivary mixture of pH>7.5) was swirled around the mouth using the tongue and cheek muscles to manipulate the oral fluid throughout the oral cavity, as described in Example III. The subject repeated this two-step procedure once a day over the course of 14 consecutive days. The change in whiteness value determined using a Vita Shade Guide was greater than 7 shades. The subject commented on how clean and fresh his mouth felt, and how long such a feeling endured. The dental examiner observed a marked reduction in the amount of plaque and food debris in the oral cavity subsequent to the two-step procedure. The dental examiner also noted visibly improved gingiva (gums). The dental examiner also noted early signs of remineralization. Previously observed trouble spots showing net mineral loss, which had been visualized as e.g., porosity, white-spot lesions, caries lesions, and/or cavitation, were noticeably improved after only 14 days, with deposition of nanoparticle hydroxyapatite on demineralized enamel surfaces visible after treatment. Longer treatment periods may produce more marked improvements in the degree of tooth mineralization.

Example VII

Maintenance of Teeth Whitening with Use of the Two-Step Combination Treatment

This example describes an embodiment useful for maintaining a degree of previously achieved teeth whitening, and for cleansing and disinfecting the oral cavity. The compositions and procedures of this example, are also well suited for those with hypersensitivity as well as those that are considered "good maintainers", i.e., those subjects with little or no plaque (biofilm). Similar to the above examples, a two-step process is utilized that incorporates two discrete compositions: Composition #1, a "Spray Whitener"; and Composition #2 a Post-Treatment Powder Oral Rinse. The composite is referred to in this example as a "Maintenance Kit".

Composition #1: Spray Whitener (Kit Component #1)

| INGREDIENT | AMOUNT |
| --- | --- |
| Hydrogen Peroxide solution (ca 25%) FMC | 82 grams |
| Deionized Purified Water | 82 gram |

An aqueous solution of 25% hydrogen peroxide was prepared by mixing 50 grams of 50% hydrogen peroxide with 50 grams deionized water. A 35 ml metal canister having the inside portion of the canister lined with polyethylene film was charged with 25 g of this 25% hydrogen peroxide solution, and then the mouthpiece-sprayhead assembly was put in place, similar to that shown in FIG. 1.

Composition #2: Powder Oral Rinse (Kit Component #2)

| INGREDIENT | AMOUNT |
| --- | --- |
| Xylitol | 85 kg |
| Sodium Bicarbonate | 7.2 kg |
| Silica (JM Huber ZEODENT 113) | 5.1 kg |
| Citric Acid | 1.1 kg |
| Menthol | 0.06 kg |
| Bubble gum Flavor (anhydrous powder) | 0.01 kg |
| Nano-hydroxyapatite | 0.5 kg |

"Kit" Maintenance Protocol

The subject had recently had professional teeth whitening performed and was satisfied with the color of her teeth. The subject desired to maintain this level of whiteness. Once-a-day treatment of the "Kit" protocol, and also at least once a day treatment after (snacks, coffee or a meal) utilizing the Powder Oral Rinse (Composition #2). In the midday, after lunch, the subject carried out the spray whitening operation as described in Example 1. Immediately after expulsion of the salivary mixture, 2 grams of the Powder Oral Rinse (Composition #2), including remineralization agent as described in Example VII, was poured directly onto tongue, and the lips subsequently sealed, and then the oral salivary mixture (the effervescent powder immediately dissolves to form a salivary mixture of pH>7.5) was swirled around the mouth using the tongue and cheek muscles to manipulate the oral fluid throughout the oral cavity. After about one minute, the salivary mixture was swallowed. The subject repeated this two-step procedure once a day over the course of thirty consecutive days. The subject also used the Powdered Oral Rinse (Composition #2) alone in between 'kit' treatments at least once a day (in addition to the "Kit" employment). The change in whiteness value determined using a Vita Shade Guide was negligible or slightly whiter.

Example VIII

Replacement of Chlorhexidine Therapy Using the Two-Step 'Kit' Treatment

This example illustrates utility of the two-step 'kit' as a replacement for chlorhexidine therapy. The patient presented to the Periodontist with symptoms of an early to moderately developed stage of periodontal disease (slightly red, slightly swollen soft tissue, bleeding upon probing, severe halitosis). The patient was prescribed the two-step treatment as described in Example III. The patient followed the prescribed protocol and returned to the Periodontist a week later. Most, if not all, of the symptoms of his periodontal disease had improved.

Example IX

Effectiveness of the Two-Step Combination Treatment in Prepping for a Dental Hygiene Prophylaxis Treatment This example describes use of the two-step protocol in prepping for a prophylaxis treatment (typically performed by a licensed dental hygienist), referred to herein as "Pre-Prophy" Treatment. The two-step protocol of Example III was carried out immediately before the prophylaxis treatment. The dental hygienist noted that the plaque and calculus debris were dislodged much easier. The patient observed that her mouth felt fresher than usual and she also noted how white her teeth appeared. She indicated that her experience was much improved to that without this "Pre-Prophy" Treatment.

Example X

Comparison of One and Two Step Protocols for Teeth Whitening

A group of 15 subjects used the spray of Example I (one-step group) once a day for 7 days, and another group followed the two step protocol of Example III (two-step group). The one-step group had an overall whitening shade change value of about 1.5-2.0 average shade change, and the two-step group had an average shade change of about 2.5-3.0 shade levels (per Vita Shade Guide). It is concluded that the use of the post-treatment rinse as a second step significantly enhances the teeth whitening result.

The foregoing Detailed Description of exemplary and preferred embodiments is presented for purposes of illustration and disclosure in accordance with the requirements of the law. It is not intended to be exhaustive nor to limit the invention to the precise form or forms described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising step(s) for . . . ."

What is claimed is:

1. A kit for two-step teeth whitening and oral hygiene, the kit comprising:
   a container comprising a mouthpiece, a spray nozzle and an actuator;
   an aqueous solution within the container, the solution comprising greater than or equal to 6% hydrogen peroxide by weight, wherein upon actuation, the mouthpiece and nozzle are configured to deliver onto the surface of the teeth and adjacent soft tissue an aerosol comprising the solution, such that the hydrogen peroxide causes teeth whitening, without discomfort or damage to soft tissues in the mouth; and
   a powder formulation comprising xylitol and a core composition comprising a carbon dioxide source, an adsorbent composition, and an acid, wherein the xylitol is present in an excess of at least 3 parts xylitol to 1 part core composition.

2. The kit of claim 1, further comprising instructions for using the two-step kit.

3. The kit of claim 1, wherein the carbon dioxide source in the core composition is selected from lithium carbonate, lithium bicarbonate, sodium carbonate, sodium bicarbonate, potassium carbonate, potassium bicarbonate, calcium carbonate, magnesium carbonate, ammonium carbonate and ammonium bicarbonate, and combinations thereof.

4. The kit of claim 3, wherein the carbon dioxide source in the core composition is sodium bicarbonate.

5. The kit of claim 1, wherein the adsorbent composition in the core composition is a metal oxide or salts thereof.

6. The kit of claim 5, wherein the metal oxide is selected from silicon dioxide (silica), aluminum oxide (alumin), aluminosilicate and zirconium silicate (zircon), and salts and combinations thereof.

7. The kit of claim 5, wherein the adsorbent in the core composition is silicon dioxide (silica).

8. The kit of claim 1, wherein the acid in the core composition is selected from citric acid, tartaric acid, fumaric acid and malic acid, and combinations thereof.

9. The kit of claim 8, wherein the acid in the core composition is citric acid.

10. The kit of claim 1, wherein the powder formulation is in the form of an effervescent powder or an effervescent tablet.

11. The kit of claim 1, wherein the powder formulation further comprises a remineralization agent.

12. The kit of claim 11, wherein the remineralization agent is a nanomaterial comprising hydroxyappetite crystals on nanoparticles.

13. The kit of claim 1, wherein the powder formulation further comprises additional ingredients.

14. The kit of claim 13, wherein at least some of the additional ingredients comprise flavoring agents.

15. A powder formulation for promoting oral hygiene, the powder formulation comprising xylitol and a core composition comprising a carbon dioxide source, an adsorbent composition, and an acid, wherein the xylitol is present in an excess of at least 3 parts xylitol to 1 part core composition.

16. A method of treatment, comprising;
   administering into the oral cavity a powder formulation comprising xylitol and a core composition comprising a carbon dioxide source, an adsorbent composition, and an acid, wherein the xylitol is present in an excess of at least 3 parts xylitol to 1 part core composition.

17. The method of claim 16, wherein administering the powder formulation is used to treat early stages of periodontal diseases.

18. The method of claim 16, wherein administering the powder formulation is used used as a pre-treatment for gum surgery.

19. The method of claim 16, wherein administering the powder formulation is used used as a pre-treatment for dental prophylaxis.

20. The method of claim 16, wherein administering the powder formulation is used used as a post-treatment for dental prophylaxis.

21. The method of claim 16, wherein administering the powder formulation is used used to reduce bacterial count in the oral cavity.

* * * * *